United States Patent
Greco et al.

(10) Patent No.: US 11,052,086 B2
(45) Date of Patent: Jul. 6, 2021

(54) 2-ANILINOPYRIMIDINE DERIVATIVES AS THERAPEUTIC AGENTS FOR TREATMENT OF BRAIN CANCERS

(71) Applicant: Beta Pharma, Inc., Wilmington, DE (US)

(72) Inventors: Michael Nicholas Greco, Lansdale, PA (US); Michael John Costanzo, Warminster, PA (US); Michael Alan Green, Easton, PA (US); Jirong Peng, Mequon, WI (US); Victoria Lynn Wilde, Montclair, NJ (US); Don Zhang, Princeton, NJ (US)

(73) Assignee: BETA PHARMA, INC., Wilmington, DE (US)

( * ) Notice: Subject to any disclaimer, the term of this patent is extended or adjusted under 35 U.S.C. 154(b) by 0 days.

(21) Appl. No.: 16/300,949

(22) PCT Filed: May 11, 2017

(86) PCT No.: PCT/US2017/032066
§ 371 (c)(1),
(2) Date: Nov. 12, 2018

(87) PCT Pub. No.: WO2017/197062
PCT Pub. Date: Nov. 16, 2017

(65) Prior Publication Data
US 2019/0365755 A1 Dec. 5, 2019

Related U.S. Application Data

(60) Provisional application No. 62/334,830, filed on May 11, 2016.

(51) Int. Cl.
*A61K 31/506* (2006.01)
*A61P 35/04* (2006.01)

(52) U.S. Cl.
CPC ............ *A61K 31/506* (2013.01); *A61P 35/04* (2018.01)

(58) Field of Classification Search
None
See application file for complete search history.

(56) References Cited

U.S. PATENT DOCUMENTS

| 2012/0316135 A1 | 12/2012 | Dalgarno et al. |
| 2013/0053409 A1 | 2/2013 | Butterworth et al. |
| 2015/0018369 A1 | 1/2015 | Stella et al. |

FOREIGN PATENT DOCUMENTS

| CN | 105461695 A | | 4/2016 | |
| CN | 105085489 B | * | 3/2019 | ........... C07D 403/14 |
| WO | 2015195228 | | 12/2015 | |
| WO | 2016029839 A1 | | 3/2016 | |
| WO | 2016094821 A2 | | 6/2016 | |

OTHER PUBLICATIONS

Addeo et al. "Erlotinib: early clinical development in brain cancer," Expert Opinion on Investigational Drugs 2014 23:7, 1027-1037; (Year: 2014).*
Porta et al. "Brain metastases from lung cancer responding to erlotinib: the importance of EGFR mutation," European Respiratory Journal 2011; 37: 624-631. (Year: 2011).*
CN-105085489-B Translation from Google (Year: 2015).*
Venur et al., "Targeted Therapy in Brain Metastases: Ready for Primetime?" American Society of Clinical Oncology (2016); 36: e123-e130.
International Search Report for International Application No. PCT/US2017/32066 filed on May 11, 2017; dated Aug. 7, 2017; 3 pages.
Written Opinion for International Application No. PCT/US2017/32066 filed on May 11, 2017; dated Aug. 7, 2017; 9 pages.

* cited by examiner

*Primary Examiner* — Jeffrey S Lundgren
*Assistant Examiner* — Michael J Schmitt
(74) *Attorney, Agent, or Firm* — Cantor Colburn LLP

(57) ABSTRACT

Methods of using substituted 2-anilinopyrimidine derivatives, and pharmaceutically acceptable salts, solvates, or compositions, for the treatment of brain cancers, in particular EGFR-mediated metastatic brain cancer, are disclosed.

7 Claims, 2 Drawing Sheets

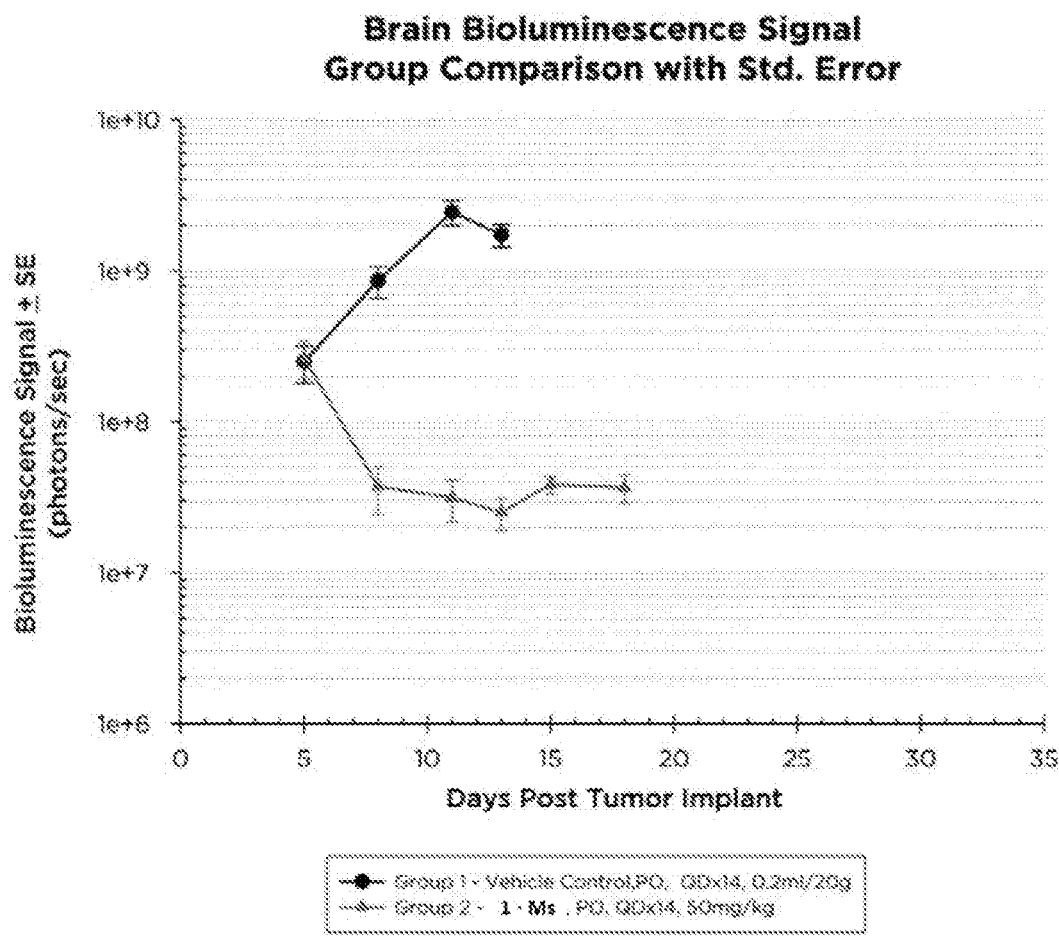
Figure 1. Brain Tumor BLI Signal Group comparisons.

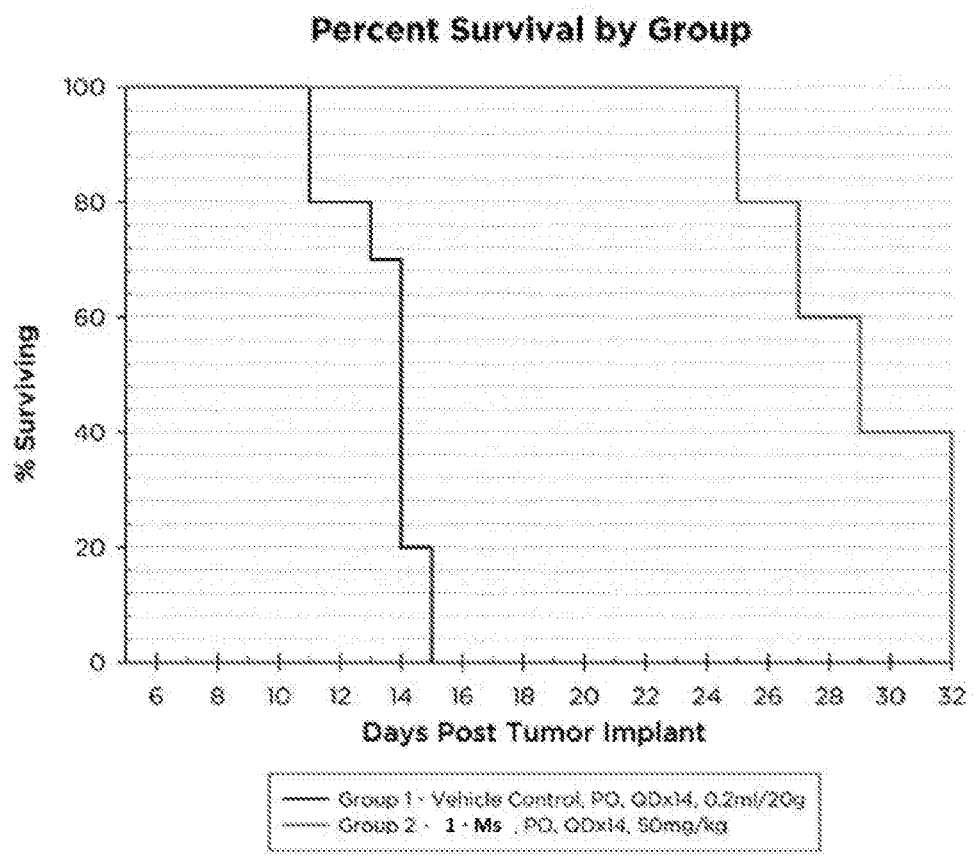
Figure 2. Percent survival by group.

2-ANILINOPYRIMIDINE DERIVATIVES AS THERAPEUTIC AGENTS FOR TREATMENT OF BRAIN CANCERS

CROSS-REFERENCE TO RELATED APPLICATIONS

This application is the U.S. national phase application of International Patent Application No. PCT/US2017/032066, filed on May 11, 2017, which claims priority benefit under 35 U.S.C. § 119(e) of U.S. Provisional Patent Application No. 62/334,830, filed May 11, 2016, the disclosures of both of which are incorporated herein by reference in their entireties.

FIELD OF THE INVENTION

The present invention relates to a method of treating EGFR-mediated metastatic brain cancer with 2-anilinopyrimidine derivatives, and pharmaceutically acceptable salts and compositions thereof.

BACKGROUND OF THE INVENTION

The epidermal growth factor receptor (EGFR, Her1, ErbB1) is a principal member of the ErbB family of four structurally-related cell surface receptors with the other members being Her2 (Neu, ErbB2), Her3 (ErbB3) and Her4 (ErbB4). EGFR exerts its primary cellular functions though its intrinsic catalytic tyrosine protein kinase activity. The receptor is activated by binding with growth factor ligands, such as epidermal growth factor (EGF) and transforming growth factor-alpha (TGF-α), which transform the catalytically inactive EGFR monomer into catalytically active homo- and hetero-dimers. These catalytically active dimers then initiate intracellular tyrosine kinase activity, which leads to the autophosphorylation of specific EGFR tyrosine residues and elicits the downstream activation of signaling proteins. Subsequently, the signaling proteins initiate multiple signal transduction cascades (MAPK, Akt and JNK), which ultimately mediate the essential biological processes of cell growth, proliferation, motility and survival.

EGFR is found at abnormally high levels on the surface of many types of cancer cells and increased levels of EGFR have been associated with advanced disease, cancer spread and poor clinical prognosis. Mutations in EGFR can lead to receptor overexpression, perpetual activation or sustained hyperactivity and result in uncontrolled cell growth, i.e. cancer. Consequently, EGFR mutations have been identified in several types of malignant tumors, including metastatic lung, head and neck, colorectal and pancreatic cancers. In lung cancer, mutations mainly occur in exons 18 to 21, which encode the adenosine triphosphate (ATP)-binding pocket of the kinase domain. The most clinically relevant drug-sensitive EGFR mutations are deletions in exon 19 that eliminate a common amino acid motif (LREA) and point mutations in exon 21, which lead to a substitution of arginine for leucine at position 858 (L858R). Together, these two activating mutations account for nearly 85% of the EGFR mutations observed in lung cancer. Both mutations have perpetual tyrosine kinase activity and as a result they are oncogenic. In at least 50% of patients who are initially responsive to current therapy, disease progression is associated with the development of a secondary mutation, T790M in exon 20 of EGFR (referred to as the gatekeeper mutation).

Approximately 30-50% of non-small cell lung cancer patients develop brain metastases (BM) (Baik, C. S.; J. Thorac. Oncol. 2015, 10, 1268), but currently no effective therapy is available for their treatment.

SUMMARY OF THE INVENTION

The present invention, in one aspect, provides a method of treating brain cancers in a subject, comprising administering to the subject a therapeutically effective amount of a compound of formula (I):

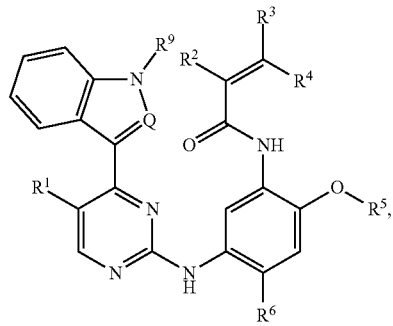

(I)

or a pharmaceutically acceptable salt, solvate or prodrug thereof, wherein:

$R^1$ is selected from hydrogen, halogen, methyl, trifluoromethyl, and cyano;

$R^2$, $R^3$, and $R^4$ are the same or different and are independently selected from hydrogen, halogen, and trifluoromethyl;

$R^5$ is selected from lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are independently selected from hydrogen and lower alkyl;

$R^6$ is selected from lower alkoxy and lower alkyl; and

Q is C—$R^{10}$ or N $R^9$ is $C_1$-$C_4$ alkyl or $C_1$-$C_4$ haloalkyl; and $R^{10}$ is H or $CH_3$.

In a preferred embodiment, the compound of formula (I) is compound 1.

In another preferred embodiment, the brain cancer is a metastatic brain cancer, and more preferably a metastatic brain cancer developed from an EGFR-mediated non-small cell lung cancer.

Efficacy of 1 in mice was determined by observing tumor regression of intracranially implanted tumors from a luciferase-enabled NCI-H1975 human cell line. Efficacy was based on bioluminescence imaging (BLI) data coupled with traditional survival endpoints. A life-span increase of greater than 100% was observed for animals treated with 1 vs. those treated with vehicle.

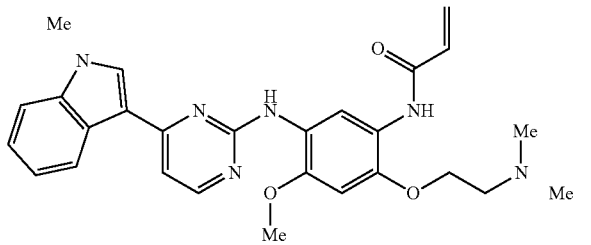

Other aspects or benefits of the present invention will be reflected in the following drawings, detailed description, and claims.

BRIEF DESCRIPTION OF THE DRAWINGS

FIG. 1 illustrates Brain Tumor BLI Signal Group comparison between treatment with 1•Ms and a vehicle control.

FIG. 2 illustrates percent survival rates by group, comparing 1•Ms treatment with a vehicle control.

DETAILED DESCRIPTION OF THE INVENTION

In one aspect, the present invention provides a method of treating brain cancer in a subject, comprising administering to the subject a therapeutically effective amount of a compound of formula (I):

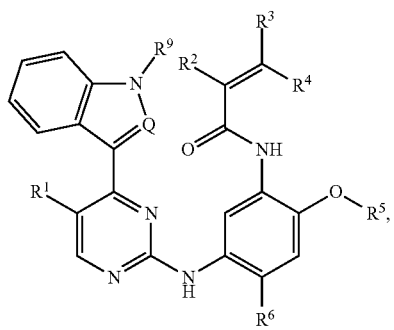

(I)

or a pharmaceutically acceptable salt, solvate, prodrug, or composition thereof, wherein:

$R^1$ is selected from hydrogen, halogen, methyl, trifluoromethyl, and cyano;

$R^2$, $R^3$, and $R^4$ are the same or different and are independently selected from hydrogen, halogen, and trifluoromethyl;

$R^5$ is selected from lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are independently selected from hydrogen and lower alkyl;

$R^6$ is selected from lower alkoxy and lower alkyl; and

Q is C—$R^{10}$ or N $R^9$ is $C_1$-$C_4$ alkyl or $C_1$-$C_4$ haloalkyl; and $R^{10}$ is H or $CH_3$.

In one embodiment of this aspect, in the compound of formula (I), Q is C—$R^{10}$.

In another embodiment of this aspect, in the compound of formula (I), $R^5$ is selected from $C_1$-$C_6$ alkyl substituted or unsubstituted azetidinyl, substituted or unsubstituted pyrrolidinyl, substituted or unsubstituted piperidinyl, $R^7R^8N$—$(CH_2)_n$— (n=1 to 5), $R^7R^8N$—$(C_3$-$C_6$ cycloalkyl)-$(CH_2)_m$— (m=1 to 3), wherein $R^7$ and $R^8$ are the same or different and are independently selected from hydrogen and lower alkyl.

In another embodiment of this aspect, in the compound of formula (I), $R^5$ is selected from methyl, $R^7R^8N$—$(CH_2)_n$— (n=2 or 3), 1-(dimethylamino)-cyclopropylmethyl, 3-(dimethylamino)cyclobutyl, 1-methylazetidin-3-yl, (R)-1-methylpyrrolidin-3-yl, (S)-1-methylpyrrolidin-3-yl, and 1-methylpiperidin-4-yl.

In another embodiment of this aspect, in the compound of formula (I), $R^5$ is 2-dimethylamino-ethyl [$(CH_3)_2NCH_2CH_2$—].

In another embodiment of this aspect, in the compound of formula (I), $R^1$ is hydrogen or halogen, or methyl.

In another embodiment of this aspect, in the compound of formula (I), $R^1$ is hydrogen.

In another embodiment of this aspect, in the compound of formula (I), $R^2$ is hydrogen or halogen.

In another embodiment of this aspect, in the compound of formula (I), $R^4$ is hydrogen.

In another embodiment of this aspect, in the compound of formula (I):

$R^2$ is hydrogen, F, or Cl;

$R^3$ is hydrogen, F, Cl, or —$CF_3$; and $R^4$ is hydrogen.

In another embodiment of this aspect, in the compound of formula (I), $R^1$, $R^2$, $R^3$, and $R^4$ are all hydrogen.

In another embodiment of this aspect, the compound of formula (I) is further characterized by a structure of formula (II):

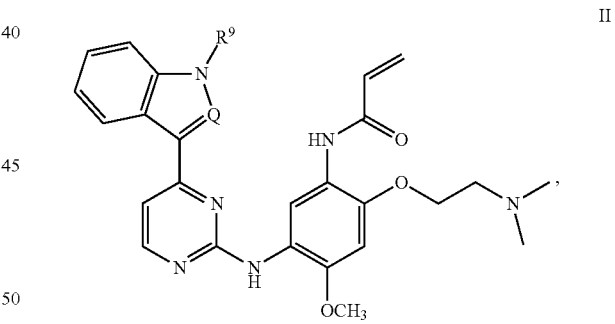

II wherein:

Q is C—$R^{10}$ or N $R^9$ is $CH_3$ or $CH_2CH_2F$; and $R^{10}$ is H or $CH_3$.

In another embodiment of this aspect, in the compound of formula (II), Q is C—$R^{10}$.

In another embodiment of this aspect, in the compound of formula (II), $R^9$ is $CH_3$.

In another embodiment of this aspect, in the compound of formula (II), Q is CH.

In a preferred embodiment of this aspect, the compound of formula (I) is further characterized by a structure of formula:

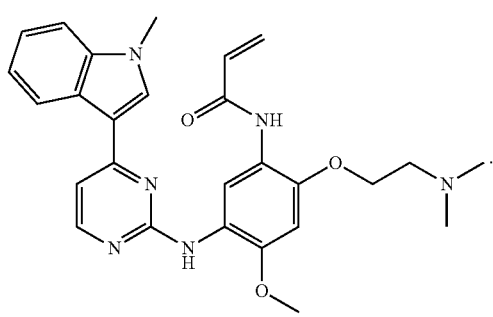

1

In another preferred embodiment of this aspect, the compound of formula (I) is a pharmaceutically acceptable salt of the compound 1.

In another preferred embodiment of this aspect, the compound of formula (I) is a methanesulfonic acid salt of the compound 1, i.e., 1·Ms.

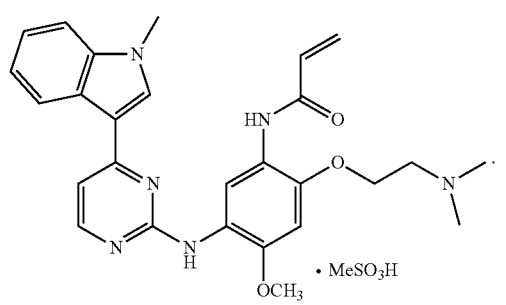

1·Ms

In another embodiment of this aspect, the compound of formula (I) is further characterized by a structure of formula:

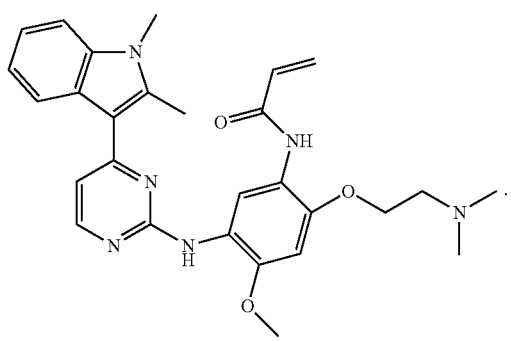

2

In another embodiment of this aspect, in the compound of formula (II), $R^9$ is $CH_2CH_2F$.

In another embodiment of this aspect, the compound of formula (I) is further characterized by a structure of formula:

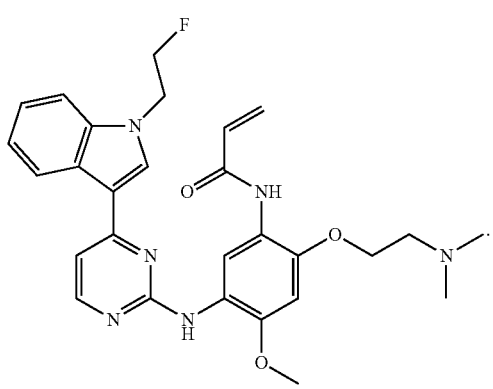

3

In another embodiment of this aspect, the compound of formula (I) is selected from the group consisting of:

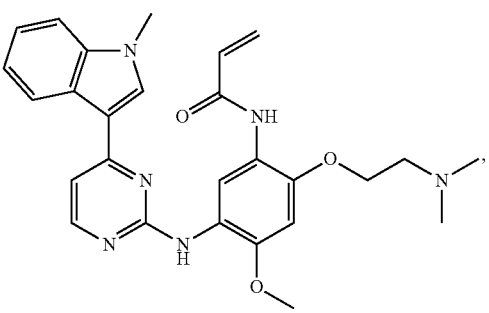

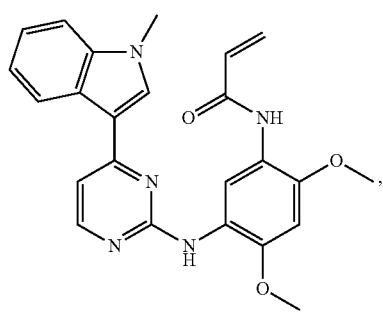

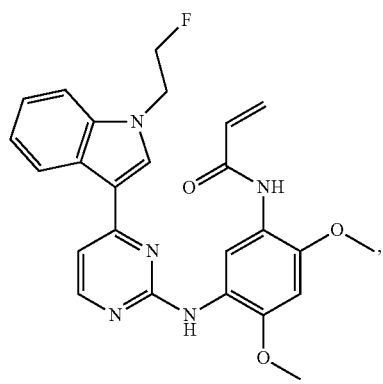

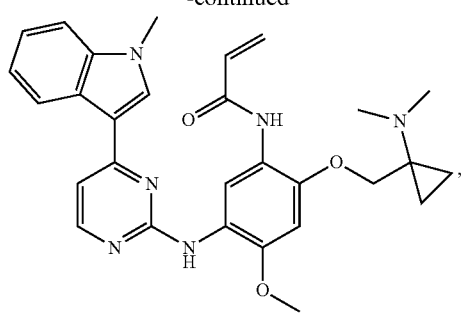
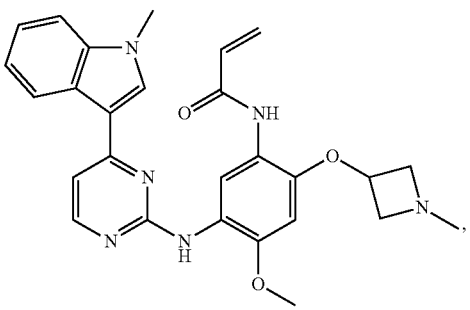
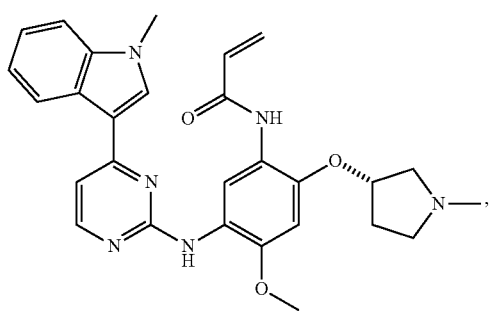
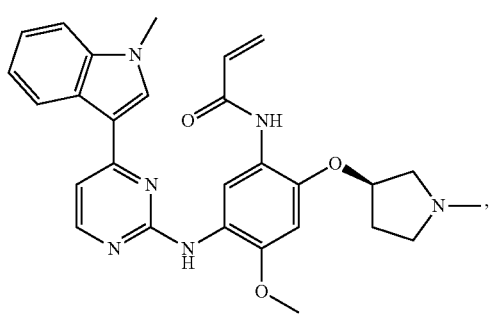
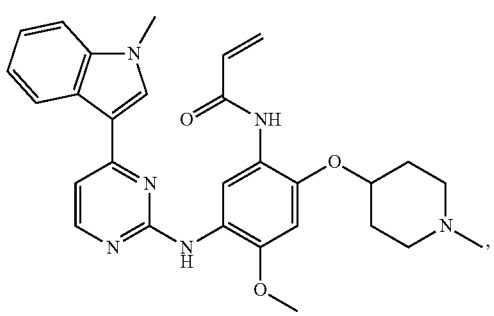
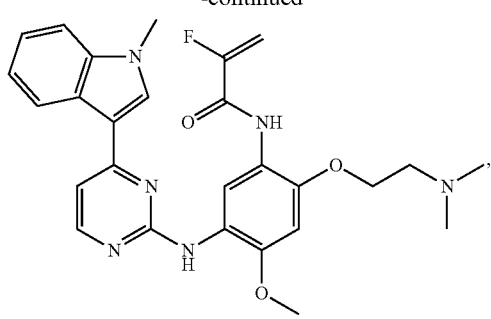
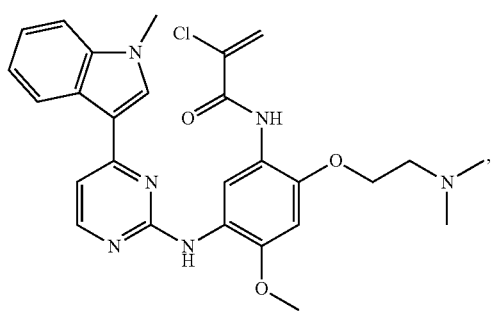
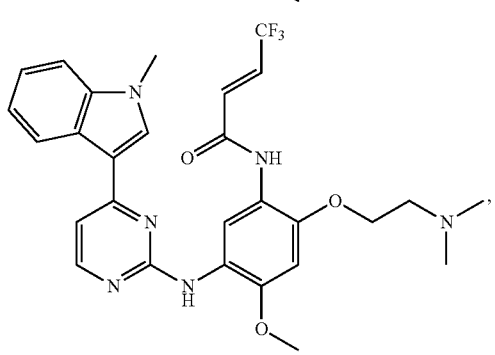
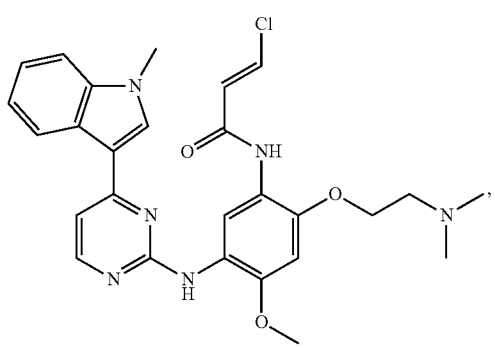
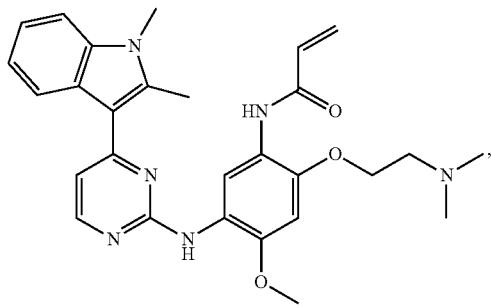

-continued
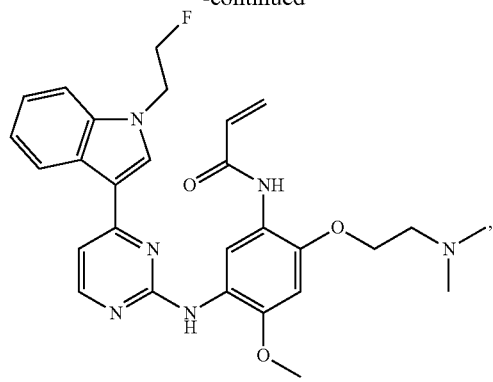
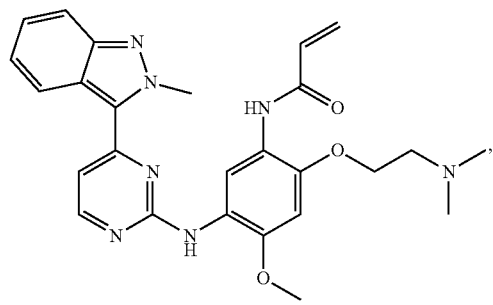
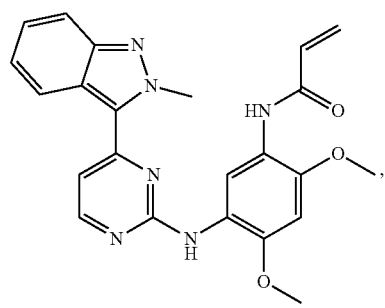
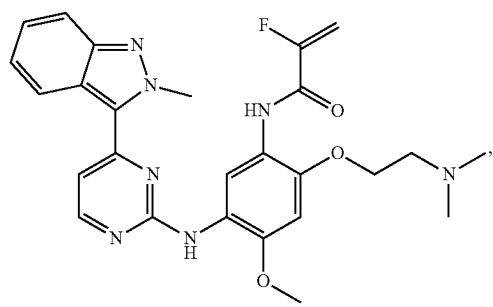
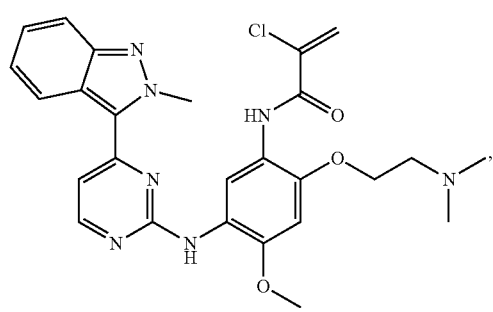
-continued
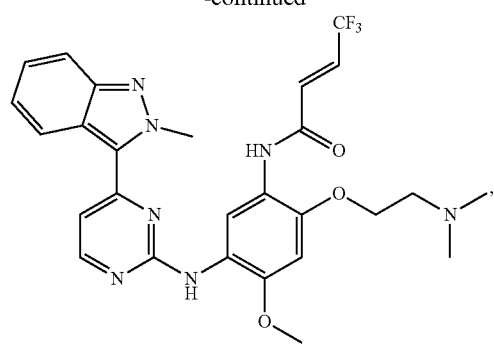
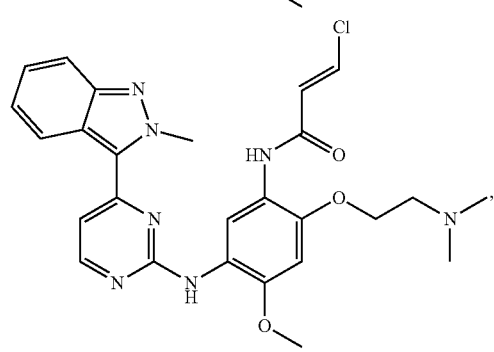
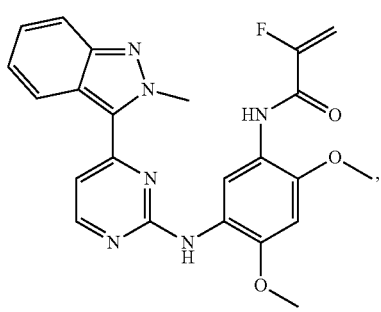
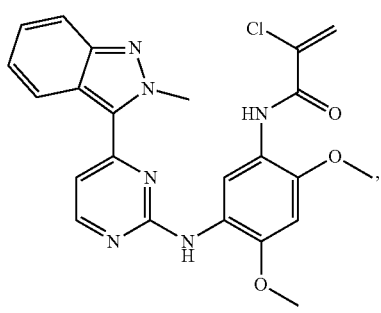
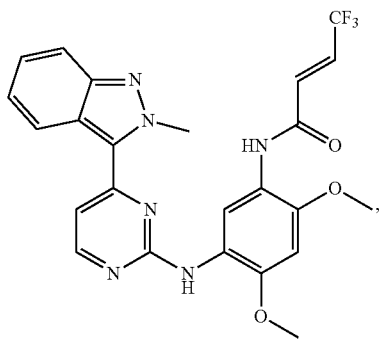

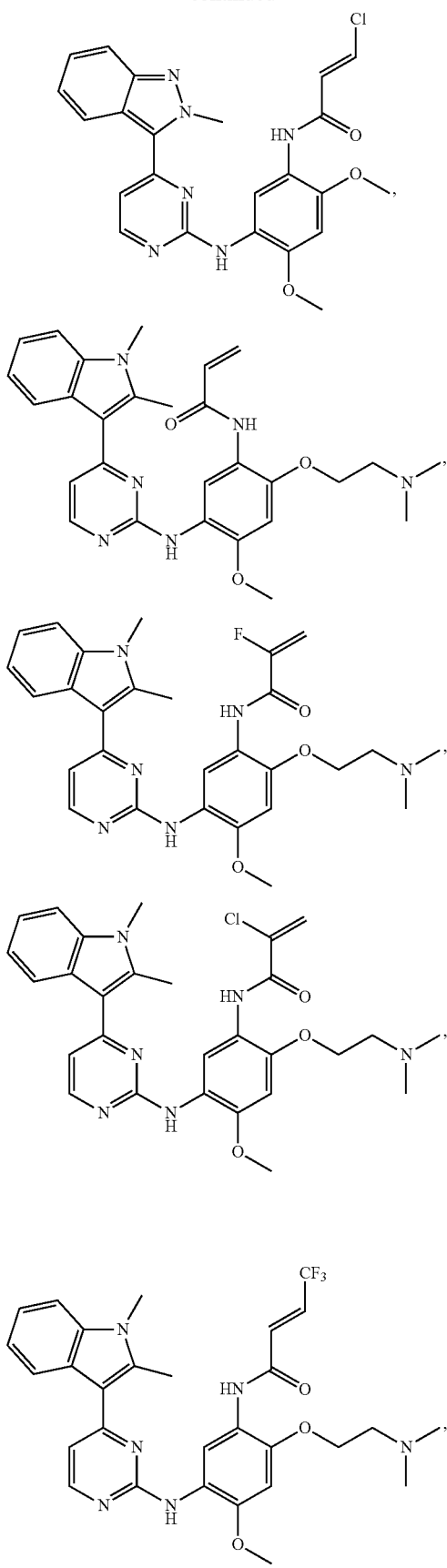

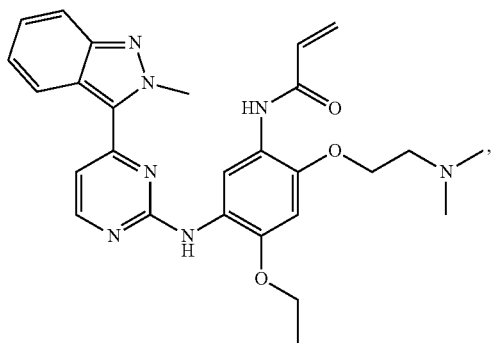
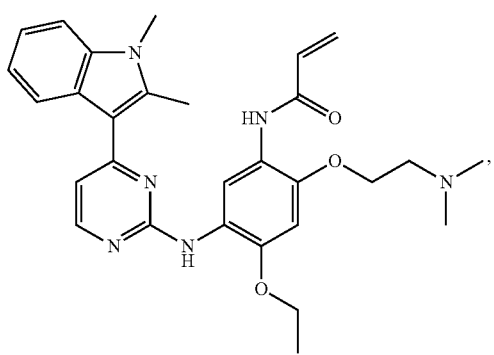
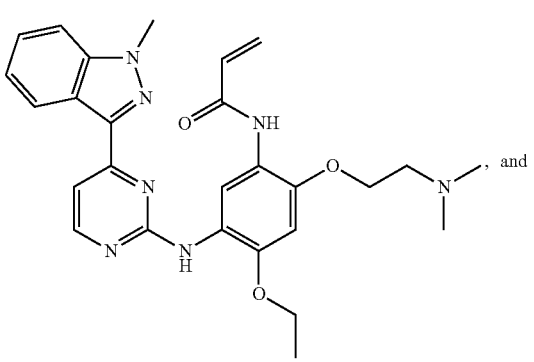
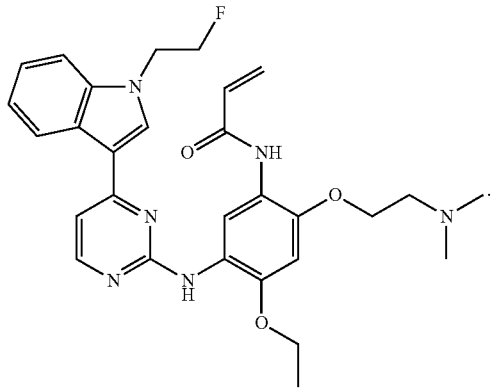
In another embodiment of this aspect, the compound of formula (I) is selected from the group consisting of:
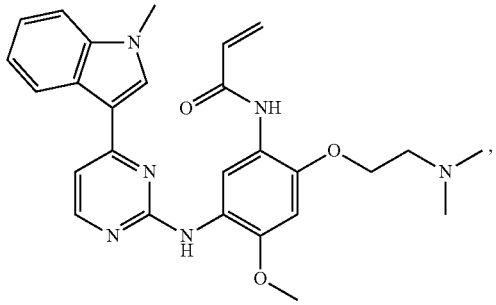
, and
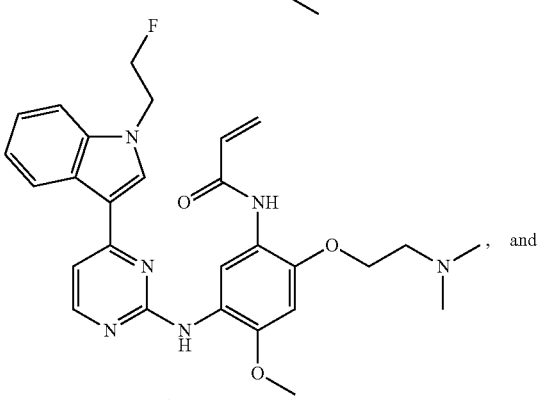
In another embodiment of this aspect, the method further comprises administering to the subject a second therapeutic agent.
In another embodiment of this aspect, the second therapeutic agent is a different EGFR modulator.

In another embodiment of this aspect, the second therapeutic agent is a chemotherapeutic agent.

In another embodiment of this aspect, said brain cancer is a metastatic brain cancer.

In a preferred embodiment of this aspect, said brain cancer is a metastatic brain cancer developed from an EGFR-mediated cancer.

In another preferred embodiment of this aspect, said brain cancer is a metastatic brain cancer developed from an EGFR-mediated non-small cell lung cancer.

In another embodiment of this aspect, the method according to any embodiment described above comprises administering to the subject a pharmaceutical composition comprising said compound of formula (I) or (II), or a pharmaceutically acceptable salt, solvate, or prodrug thereof, and a pharmaceutically acceptable carrier.

In another embodiment of this aspect, the compound of formula (I) or (II) is compound 1. In another embodiment of this aspect, the compound of formula (I) or (II) is the methanesulfonic acid salt of compound 1 (1·Ms).

In another aspect, the present invention provides use of a compound of formula (I), or a pharmaceutically acceptable salt, solvate, prodrug, or composition thereof, in the manufacture of a medicament for the treatment of brain cancer:

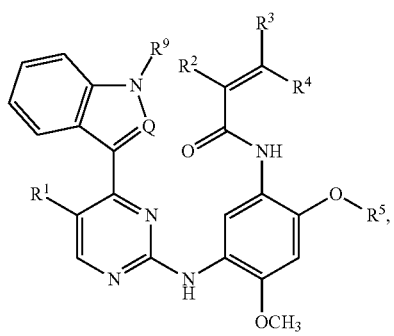

(I)

or a pharmaceutically acceptable salt, solvate, prodrug, or composition thereof, wherein:

$R^1$ is selected from hydrogen, halogen, methyl, trifluoromethyl, and cyano;

$R^2$, $R^3$, and $R^4$ are the same or different and are independently selected from hydrogen, halogen, and trifluoromethyl;

$R^5$ is selected from lower alkyl, optionally substituted 3- to 6-membered heterocyclyl, $R^7R^8$N-(lower alkyl), and $R^7R^8$N-(cycloalkylalkyl), wherein $R^7$ and $R^8$ are the same or different and are independently selected from hydrogen and lower alkyl;

$R^6$ is selected from lower alkoxy and lower alkyl; and

Q is C—$R^{10}$ or N $R^9$ is $C_1$-$C_4$ alkyl or $C_1$-$C_4$ haloalkyl; and $R^{10}$ is H or $CH_3$.

In one embodiment of this aspect, the compound of formula (I) is further characterized by a structure of formula II:

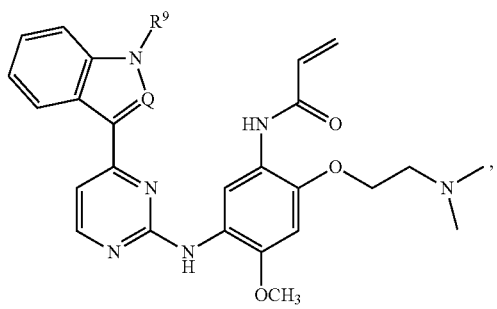

II wherein:
Q is C—$R^{10}$ or N
$R^9$ is $CH_3$ or $CH_2CH_2F$; and
$R^{10}$ is H or $CH_3$.

In another embodiment of this aspect, the compound of formula (I) is selected from the group consisting of:

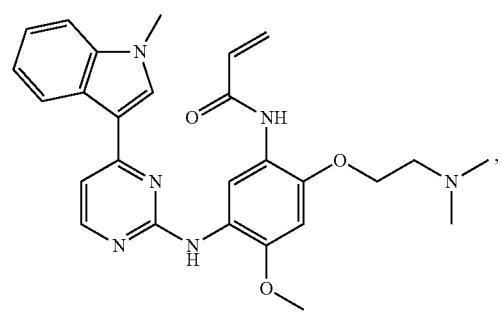

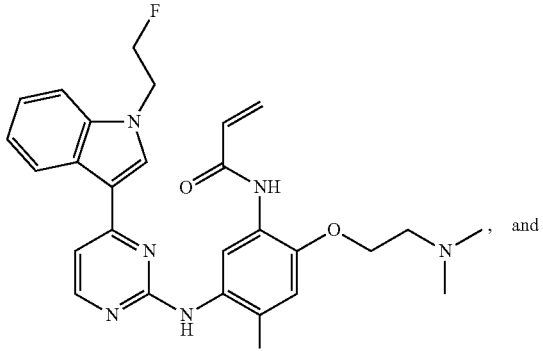

and

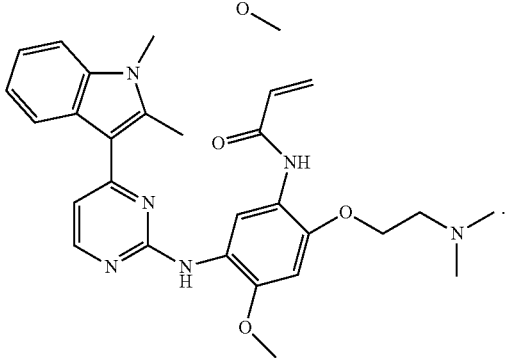

In another embodiment of this aspect, the brain cancer is a metastatic brain cancer.

In another embodiment of this aspect, the brain cancer is a metastatic brain cancer developed from an EGFR-mediated non-small cell lung cancer.

Other aspects or embodiments of the present invention include those as substantially shown and described and any possible combinations of any two or more embodiments described herein.

The terms in the present application, if not specifically defined, take their ordinary meanings as would be understood by those skilled in the art.

As used herein, the term "halo" or "halogen" refers to F, Cl, or Br.

The term "lower alkyl" refers to a branched or straight-chain alkyl group having from one to seven carbon atoms, preferably one to four, and more preferably one to two carbon atoms.

The term "lower alkoxy" refers to an alkoxy group (—OR) having from one to seven, preferably one to four, and more preferably one to two carbon atoms.

The term "cyano" refers to —CN.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

The term "solvate," as used herein, means a physical association of a compound of this invention with a stoichiometric or non-stoichiometric amount of solvent molecules. For example, one molecule of the compound associates with one or more, preferably one to three, solvent molecules. It is also possible that multiple (e.g., two) molecules of the compound share one solvent molecule. This physical association may include hydrogen bonding. In certain instances the solvates will be capable of isolation as crystalline solid. The solvent molecules in the solvate may be present in a regular arrangement and/or a non-ordered arrangement. Exemplary solvates include, but are not limited to, hydrates, ethanolates, methanolates, and isopropanolates. Methods of solvation are generally known in the art.

The term "prodrug," as used herein, refers to a derivative of a compound that can be transformed in vivo to yield the parent compound, for example, by hydrolysis in blood. Common examples include, but are not limited to, ester and amide forms of an active carboxylic acid compound; or vice versa, an ester from of an active alcohol compound or an amide form of an active amine compound. Such amide or ester prodrug compounds may be prepared according to conventional methods as known in the art. For example, a prodrug of a compound of formula II of the present invention could be in the form of the following formula III:

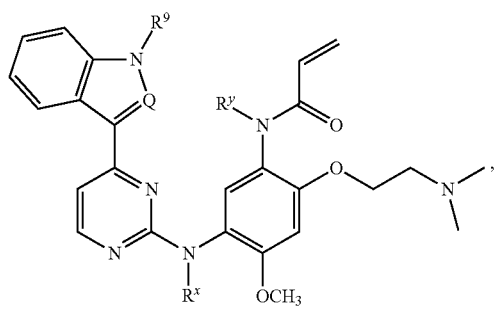

wherein Rx and $R^Y$ are independently H and —C(O)—R, wherein R is $C_1$-$C_4$ alkyl, preferably methyl or ethyl, and more preferably methyl. Other prodrugs of the present invention can be prepared similarly.

When it is possible that, for use in therapy, therapeutically effective amounts of a compound of the present invention, or pharmaceutically acceptable salts or solvates thereof, may be administered as the raw chemical, it is possible to present the active ingredient as a pharmaceutical composition. Accordingly, the disclosure further provides pharmaceutical compositions, which include any compounds of the present invention, or pharmaceutically acceptable salts or solvates thereof, and one or more, preferably one to three, pharmaceutically acceptable carriers, diluents, or other excipients. The carrier(s), diluent(s), or other excipient(s) must be acceptable in the sense of being compatible with the other ingredients of the formulation and not deleterious to the subject being treated.

Pharmaceutical formulations may be presented in unit dose forms containing a predetermined amount of active ingredient per unit dose. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the compositions of this disclosure comprise a combination of a compound of the present disclosure and one or more, preferably one or two, additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

It should be understood that in addition to the ingredients particularly mentioned above, the formulations may include other agents conventional in the art having regard to the type of formulation in question, for example those suitable for oral administration may include flavoring agents.

The term "patient" or "subject" includes both human and other mammals.

The term "mammal" or "mammalian animal" includes, but is not limited to, humans, dogs, cats, horses, pigs, cows, monkeys, rabbits and mice. The preferred mammals are humans.

The term "therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, or other factors of the subject to be treated. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "treating" or "treatment" refers to: (i) inhibiting the disease, disorder, or condition, i.e., arresting its development; (ii) relieving the disease, disorder, or condition, i.e., causing regression of the disease, disorder, and/or condition; or (iii) preventing a disease, disorder or condition from occurring in a subject that may be predisposed to the disease, disorder, and/or condition but has not yet been diagnosed as having it. Thus, in one embodiment, "treating" or "treatment" refers to ameliorating a disease or disorder, which may include ameliorating one or more physical parameters, though maybe indiscernible by the subject being treated. In another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

When the term "about" is applied to a parameter, such as amount, temperature, time, or the like, it indicates that the parameter can usually vary by ±10%, preferably within ±5%, and more preferably within ±2%. As would be understood by a person skilled in the art, when a parameter is not critical, a number provided in the Examples is often given only for illustration purpose, instead of being limiting.

The term "a," "an," or "the," as used herein, represents both singular and plural forms. In general, when either a singular or a plural form of a noun is used, it denotes both singular and plural forms of the noun.

The following non-limiting Examples further illustrate certain aspects of the present invention.

EXAMPLES

Materials and Methods

N-(2-(2-(Dimethylamino)ethoxy)-4-methoxy-5-((4-(1-methyl-1H-indol-3-yl)pyrimidin-2-yl)amino)phenyl)acrylamide methanesulfonate (1•Ms; $C_{27}H_{30}N_6O_3$·1.06 $CH_3SO_3H$. MW=486.58, FW=588.45, purity=100%) was formulated in a vehicle of 1% polysorbate 80 in water. The complete vehicle was added to the pre-weighed compound to achieve a 5 mg/mL stock solution, suitable for treatment of the 50 mg/kg dose level. The mixture was vortexed for approximately one minute resulting in a light yellow solution with a pH value of 7. The dosing solution was prepared fresh daily.

Animals

Female Envigo Nude mice (Hsd:Athymic Nude-Foxn1$^{nu}$) were used. They were 6-7 weeks old on Day 1 of the experiment. The animals were fed irradiated Harlan 2918.15 Rodent Diet and water ad libitum. Animals were housed in static cages with Bed-O'Cobs™ bedding inside Biobubble® Clean Rooms that provide H. E. P. A filtered air into the bubble environment at 100 complete air changes per hour. All treatments, body weight determinations, and tumor measurements were carried out in the bubble environment. The environment was controlled to a temperature range of 70±2 OF and a humidity range of 30-70%.

Cell Preparation

NCI-H1975-Luc cells were obtained from Clovis. They were grown in RPMI 1640 medium which was modified with 1 mM Na pyruvate+2 mM L-glutamine+10 mM HEPES+2.5 g/L glucose+5 ug/mL blasticidin and supplemented with 10% non-heat-inactivated Fetal Bovine Serum (FBS) and 1% 100× Penicillin/Streptomycin/L-Glutamine (PSG). The growth environment was maintained in an incubator with a 5% $CO_2$ atmosphere at 37° C. When expansion was complete, the cells (passage 4) were trypsinized using 0.25% trypsin-EDTA solution. Following cell detachment, the trypsin was inactivated by dilution with complete growth medium and any clumps of cells were separated by pipetting. The cells were centrifuged at 200 ref for 8 minutes at 4° C. the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna automated cell counter to determine a pre-implantation cell viability. The cell suspension was centrifuged at 200 ref for 8 minutes at 4° C. The supernatant was aspirated and the cell pellet was re-suspended in cold serum-free medium to generate a final concentration of 1.00E+08 trypan-excluding cells/mL. The cell suspension was maintained on wet ice during implantation. Following implantation, an aliquot of the remaining cells was diluted with a trypan blue solution and counted to determine the post-implantation cell viability.

Intracranial Implantation

Test mice were implanted intracranially on Day 0 with 1.00E+06 cells per 10 μL as per the protocol (Appendix 1). For aseptic surgical implantation, mice were injected with 0.2 mg/kg buprenorphine and anesthetized using 2% isoflurane in air. The mice were then secured in a stereotaxic frame (ASI instruments, Inc.) using non-rupture ear bars. Ocular ointment was applied to the eyes of the mice to prevent drying during surgery. A re-circulating 37° C. water heated pad was used to maintain the animal's body temperature during the implantation procedure. Once in the stereotaxic frame, the cranium was swabbed with alternating chlorhexidine solution and 70% ethanol-saturated swabs to disinfect the skin surface and prepare for the incision. A 1 cm longitudinal incision was made centrally over bregma of the cranium using a #15 BD scalpel blade. The incision was retracted using small, serrated serrefines. The thin layer of connective tissue covering the surface of the skull was removed using dry cotton swabs under light pressure. Bleeding vessels were cauterized to prevent blood loss. A 0.9 mm drill bit was then centered over bregma, moved 2 mm right lateral, 1 mm anterior to the coronal suture and lowered to score the surface of the skull using the stereotaxic electrode manipulator arm. The drill was removed from the stereotaxic frame and the burr hole through the skull to the surface of the dura mater was completed by hand. The cell suspension (stored on wet ice) was mixed thoroughly and drawn up into a 50 μL gas-tight Hamilton syringe. A standard 27 g needle was filled with the cell suspension to eliminate air pockets and the luer tip of the syringe was inserted into the needle hub. The syringe was secured to a custom-built syringe holder (ASI Instruments. Inc.) and attached to the stereotaxic frame manipulator arm. The syringe needle was centered over the burr hole and lowered until the beveled tip was level with the underside of the skull at the surface of the dura mater. The needle was then lowered 3 mm into the brain and retracted 1 mm to form a "reservoir" for the deposition of the cell suspension. 10 μL of the cell suspension (1×10$^6$ cells/mouse) was then injected slowly into the brain tissue with any slight leakage (typical for IC implants) being absorbed with a dry cotton swab. Following the injection, the needle was withdrawn and the burr hole was immediately sealed with bone wax to minimize the loss of implanted cells. The skull surface was then cleaned with alternating dry and 70% ethanol saturated cotton swabs to remove extraneous cells and deter extracranial tumor growth. The mouse was removed from the stereotaxic frame and the incision was closed using a stainless steel wound clip. Once the mouse regained consciousness and dorsal recumbancy, it was returned to its caging.

Treatment

All mice were sorted into treatment groups based on estimation of tumor burden via bioluminescence imaging. The mice were distributed to ensure that the mean tumor burden for all groups was within 10% of the overall mean tumor burden for the study population. Treatment began on Day 5.

Group 1: Vehicle Control (1% polysorbate 80), 0.2 mL/20 g, PO, QD×11 (once daily on Days 5-15).

Group 2: 1•Ms, 50 mg/kg, PO. QD×14 (once daily on Days 5-18).

Bioluminescence Imaging

In vivo bioluminescence imaging was performed using an IVIS 50 optical imaging (Xenogen, Alameda. Calif.). Animals were imaged three at a time under ~1-2% isoflurane gas anesthesia. Each mouse was injected IP with 150 mg/kg D-luciferin and imaged in the prone position. 10 minutes after the injection. Large binning of the CCD chip was used, and the exposure time was adjusted (2 seconds to 2 minutes) to obtain at least several hundred counts from the metastatic tumors that were observable in each mouse in the image and to avoid saturation of the CCD chip. BLI images were collected on Day 5, 8, 11, 13, 15, and 18. Images were analyzed using the Living Image version 4.3.1 (Xenogen, Alameda, Calif.) software. Fixed-volume ROIs were placed to encompass the primary tumor on prone images for each individual animal, and labeled based on animal identification. Total flux (photons/sec) was calculated and exported for all ROIs to facilitate analyses between groups.

Measurements and Endpoints

% T/C of primary tumor burden (as estimated by BLI) was used as the primary endpoint in this study. % T/C is defined as the median BLI signal of the treated group divided by the median BLI signal of the control group×100. Day 13% T/C was used for analysis because it was the last day imaging was performed and more than the median number of animals in the control group remained on study. Life span extension was used as a secondary endpoint in this study. A complete response (CR) is defined as a decrease in tumor mass (based on bioluminescence imaging) to an unreliable signal (below 2.0E+05 photons/sec). Background levels for BLI are typically in the range of 1E+03-1E+04 photons/sec. A partial response (PR) is defined as a ≥50% decrease in tumor BLI signal from that at first treatment. PRs are exclusive of CRs.

Efficacy Results

Group 2: 1•Ms, 50 mg/kg, PO, QD×14 (Once Daily on Days 5-18).

Treatment with 1•Ms produced significant (P<0.05) anticancer activity based on BLI derived Day 13% T/C (1%; FIG. 1). The median lifespan was 29.0 days (107% ILS or 15 day increase in lifespan) (p<0.001). By Day 18, 100% of animals had partial tumor regressions, and none had complete regressions (FIG. 2).

Compound 1 also effectively inhibits the kinase domain of the T790M double mutant in addition to the activating mutations and therefore overcomes the resistance observed with the currently used therapy of reversible inhibitors. Since the role of EGFR in non-small cell lung cancer (NSCLC) is well-established (Ohashi, K.; et al. *J. Clin. Oncol.* 2013, 31, 1070), 1 represents a potential therapeutic agent for the treatment of non-small cell lung cancer.

Compound 1 achieves therapeutic levels of brain concentration when dosed orally in the rat (Table 1). Furthermore, 1 was efficacious against intracranially implanted brain tumors in mice. Therefore, 1 represents a potential therapeutic agent for the treatment of EGFR-mediated metastatic brain cancer.

Treatment with 1•Ms was well-tolerated and produced significant (P<0.05) anticancer activity based on Day 13 BLI % T/C and lifespan. Although all mice eventually died of disease, life span was more than doubled by treatment with 1•Ms.

TABLE 1

Pharmacokinetic (PK) parameters for 1 · Ms in male SD rats dosed PO @ 5 mg/kg using a 0.5% methylcellulose vehicle.

| Parameter | Plasma | Brain |
|---|---|---|
| $C_{max}$ (ng/mL or ng/g) | 96.3 | 606 |
| $T_{max}$ (h) | 2.00 | 2.00 |
| $T_{1/2}$ (h) | 1.97 | 2.01 |
| $T_{last}$ (h) | 18.0 | 18.0 |
| $AUC_{0-last}$ (ng · h/mL or ng · h/g) | 535 | 5047 |
| $AUC_{0-inf}$ (ng · h/mL or ng · h/g) | 538 | 5085 |
| $MRT_{0-last}$ (h) | 5.01 | 5.95 |
| $MRT_{0-inf}$ (h) | 5.10 | 6.07 |
| $AUC_{Extra}$ (%) | 0.593 | 0.746 |
| $AUMC_{Extra}$ (%) | 2.42 | 2.57 |
| $^d$AUC Ratio | — | 9.44 |

The foregoing examples or preferred embodiments are provided for illustration purpose and are not intended to limit the present invention. Numerous variations and combinations of the features set forth above can be utilized without departing from the present invention as set forth in the claims.

What is claimed is:

1. A method of treating brain cancer in a subject, comprising administering to the subject a therapeutically effective amount of N-(2-(2-(dimethylamino)ethoxy)-4-methoxy-5-((4-(1-methyl-1H-indol-3-yl)pyrimidin-2-yl)amino)phenyl)acrylamide methanesulfonate (formula 1·Ms):

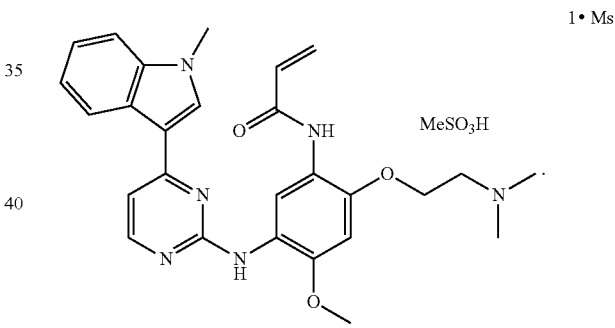

2. The method of claim 1, further comprising administering to the subject a second therapeutic agent.

3. The method of claim 2, wherein said second therapeutic agent is a different EGFR modulator.

4. The method of claim 2, wherein said second therapeutic agent is a chemotherapeutic agent.

5. The method of claim 1, wherein said brain cancer is a metastatic brain cancer.

6. The method of claim 1, wherein said brain cancer is metastatic brain cancer developed from an EGFR-mediated non-small cell lung cancer.

7. The method of claim 1, comprising administering to the subject a pharmaceutical composition comprising said N-(2-(2-(dimethylamino)ethoxy)-4-methoxy-5-((4-(1-methyl-1H-indol-3-yl)pyrimidin-2-yl)amino)phenyl)acrylamide methanesulfonate (formula 1·Ms), and a pharmaceutically acceptable carrier.

* * * * *